United States Patent [19]

Carlson-Orsi

[11] Patent Number: 5,738,640
[45] Date of Patent: Apr. 14, 1998

[54] UPPER SPINE AND NECK SUPPORT CUSHION

[76] Inventor: Diane Carlson-Orsi, 20360 Holt Ave., Covina, Calif. 91724

[21] Appl. No.: 917,160

[22] Filed: Aug. 25, 1997

Related U.S. Application Data

[63] Continuation of Ser. No. 699,926, Aug. 20, 1996, abandoned.

[51] Int. Cl.$^6$ ................................................ A61F 5/00
[52] U.S. Cl. ............................ 602/19; 602/18; 128/845
[58] Field of Search .................... 602/17–19; 128/845, 128/DIG. 19; 606/240; 5/630, 632, 636

[56] References Cited

U.S. PATENT DOCUMENTS

| | | | |
|---|---|---|---|
| D. 204,443 | 4/1966 | Wood | 5/636 |
| D. 245,537 | 8/1977 | Gurgiolo | D24/190 |
| 2,973,939 | 7/1961 | Matthewson | 602/18 |
| 3,857,388 | 12/1974 | Frankel | 602/19 |
| 4,796,315 | 1/1989 | Crew | 606/240 X |
| 4,876,755 | 10/1989 | Parrish | 5/922 |
| 5,528,784 | 6/1996 | Painter | 5/636 |

*Primary Examiner*—Richard J. Apley
*Assistant Examiner*—Denise Pothier
*Attorney, Agent, or Firm*—Edgar W. Averill, Jr.

[57] ABSTRACT

An upper spine and neck support cushion. The cushion has a generally vertical spine support pillow which is held at its top end to a generally horizontal neck support pillow. The device is held onto the wearer by a pair of straps which hold the spine support pillow against the upper portion of the wearer's spine and the neck support pillow under the user's neck. When the user is resting against a chair or bed the spine support pillow gently provides support for the upper portion of the wearer's spine and the neck support pillow provides support for the neck while the head is rested upon the chair or bed upon which the user is resting.

1 Claim, 2 Drawing Sheets

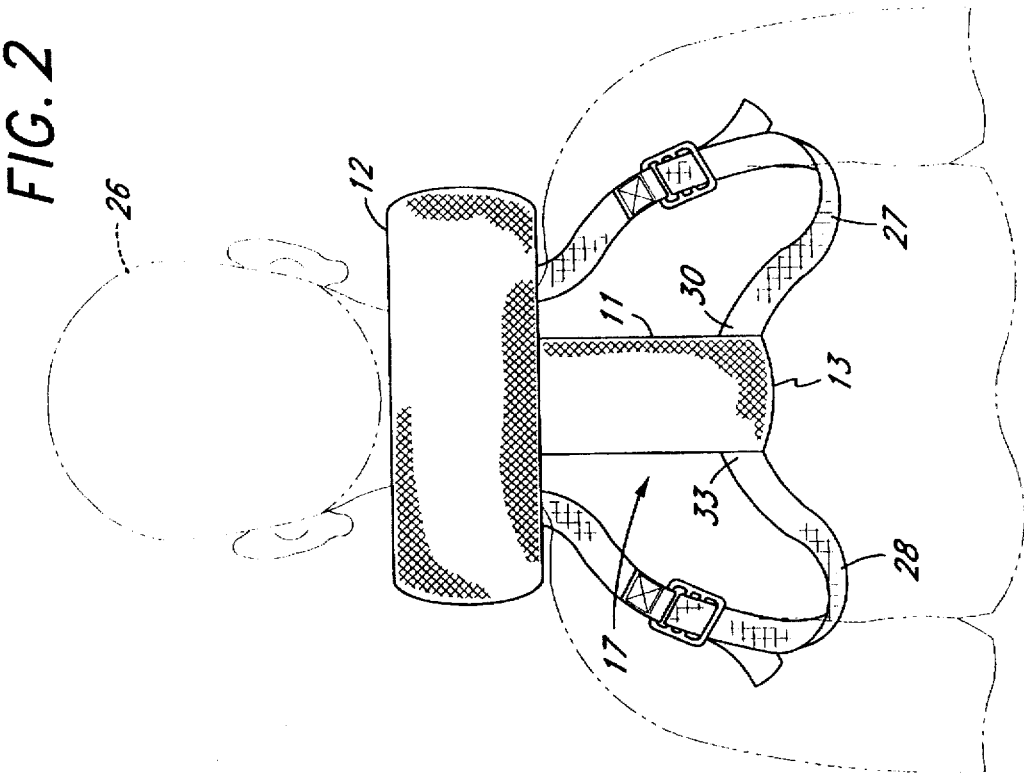
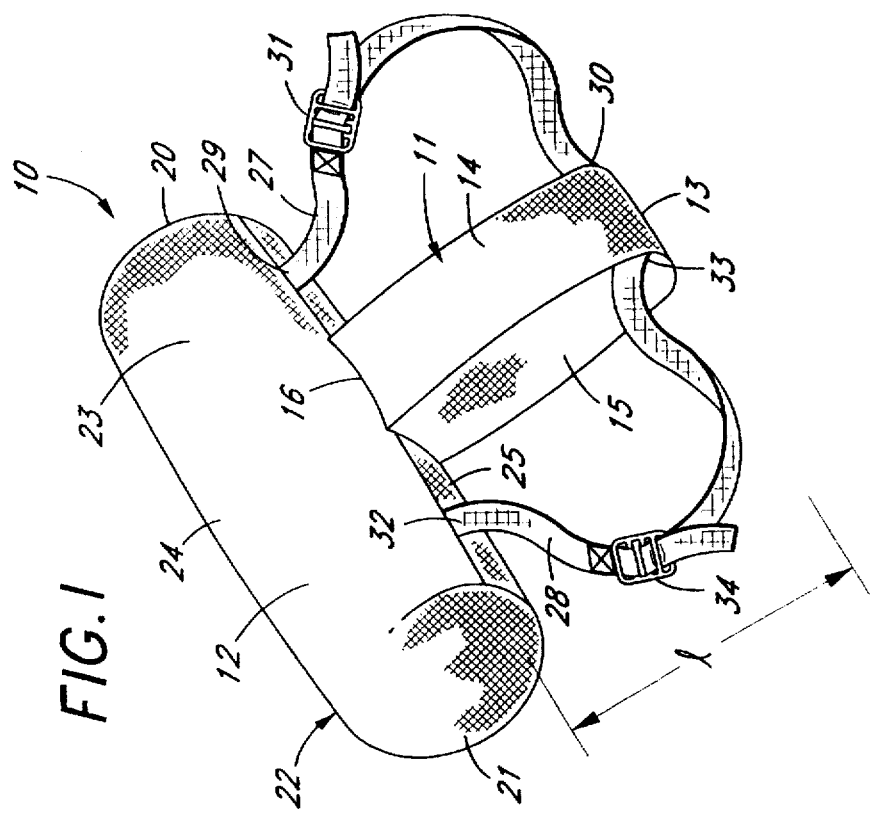

UPPER SPINE AND NECK SUPPORT CUSHION

This application is a continuation of application Ser. No. 08/699,926 filed Aug. 20, 1996, now abandoned.

BACKGROUND OF THE INVENTION

The field of the invention is orthopedic devices and the invention relates more particularly to devices for supporting and comforting a wearer's upper spine and neck when fatigued from excessive work, computer work, lifting, twisting or repetitive machine work.

Numerous devices have been devised over the years to provide comfort to a person sitting in a chair or lying in a bed. An early device is a headrest apparatus shown in U.S. Pat. No. 382,949. The headrest is held on an upright and a series of straps help to hold the headrest in a position so that the wearer can rest his head back without the need of a chair or bed.

A support for the neck and head is shown in U.S. Pat. No. 673,872. This has a inflatable air cushion generally in a U-shape which passes around the user's neck. A flat cushion is designed to be held by a snapped neck cushion and support the back of the head by the wearer.

Another device for supporting a user's head is shown in U.S. Pat. No. 2,973,030 where a frame is held to the user's shoulder and waist and supports a neck rest 50 which rests against the back of the wearer's head. The device is designed to be used by driver's or other persons who are engaged in a task that does not permit them to rest their head on a reclining chair or bed.

U.S. Pat. No. 4,679,263 shows a device which attaches around a user's head having two side cushions which cover the user's ears and a back cushion which supports the back of the user's head, the user's neck and upper spine.

After a period of time at a desk or computer it is not uncommon for a person to develop a slight pain or tightness in the user's upper back and neck. None of the prior art devices are capable of relaxing the shoulders and upper back muscles in a manner which is easy to attach and is capable of immediate relief.

BRIEF SUMMARY OF THE INVENTION

It is an object of the present invention to provide a cushion which can be easily put on and which provides immediate relaxation for the upper back, shoulders and neck of the wearer.

The present invention is for an upper spine and neck support cushion. The cushion has a generally vertical spine support pillow which has a bottom, a spine contacting surface, sides and a furniture contacting side and a top. The spine support pillow is constructed from a soft pliant material. A generally horizontal neck support pillow is attached to the top of the spine support pillow. The neck support pillow has a neck contacting surface and a furniture contacting surface, a top surface and a bottom surface, a right end and a left end, and is free of any head support means. When used, the user's head will be supported by the surface of the chair or bed upon which the user rests and not upon the neck support pillow. Means are provided for holding the upper spine and neck support cushion to the wearer. Preferably these means for holding comprise a right hand strap and a left hand strap both of which are adjustable and both of which are attached to the bottom of the spine support pillow at one end and to the neck support pillow at the other end. In this way, the cushion can be easily put on by a wearer and used for brief or extended periods of relaxation.

BRIEF DESCRIPTION OF THE DRAWINGS

FIG. 1 is a perspective view showing the front and right side of the upper spine and neck support cushion of the present invention.

FIG. 2 is a back view of the upper spine and neck support cushion of FIG. 1 shown on a wearer.

DESCRIPTION OF THE PREFERRED EMBODIMENTS

Figure 3:
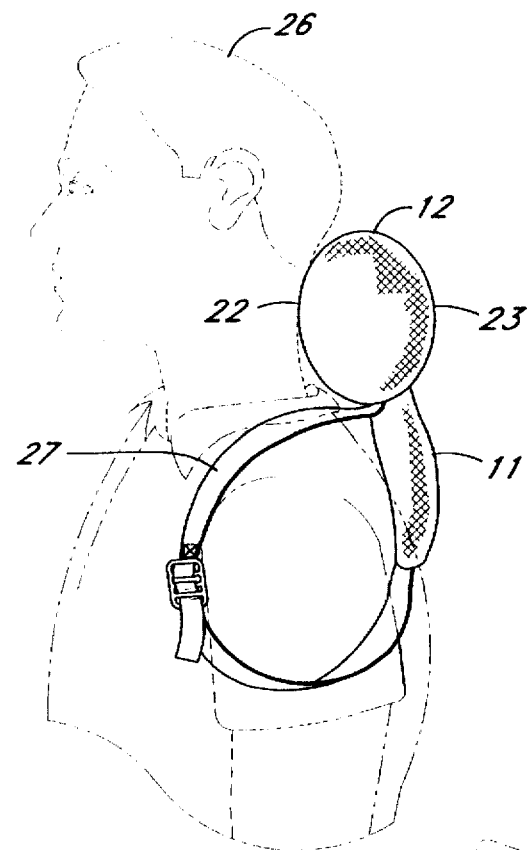
FIG. 3 is a side view of the upper spine and neck support cushion of FIG. 1 shown on a wearer in an upright position.

The upper spine and neck support cushion is shown in perspective view in FIG. 1 and indicated generally by reference character 10. Cushion 10 has a generally vertical spine support pillow portion 11 and a generally horizontal neck support pillow 12. The terms "generally horizontal" and "generally vertical" are referring to the position of the pillow when the user is upright and it is understood, of course, that these terms "generally horizontal" and "generally vertical" will change as the position of the user changes, but are used to simply aid in describing the portions of the cushion.

The generally vertical spine support pillow has a bottom 13, a length "1". Generally vertical spine support pillow 11 has a spine contacting surface 14, a furniture contacting side 15 and a top 16 which is attached to the generally horizontal neck support pillow 12. The spine support pillow is between about 4" and 6" in length and is preferably about 8" in length and is a generally flattened cylindrical or eliptical shape having an uncompressed thickness of about 2–3" and a width of about 3–4". It can be made from any soft pliable material such as used in pillows or could be air filled flexible sheeting. Alternatively, it could be made from a heat retaining material to provide the additional benefit of a warming action.

Figure 4:
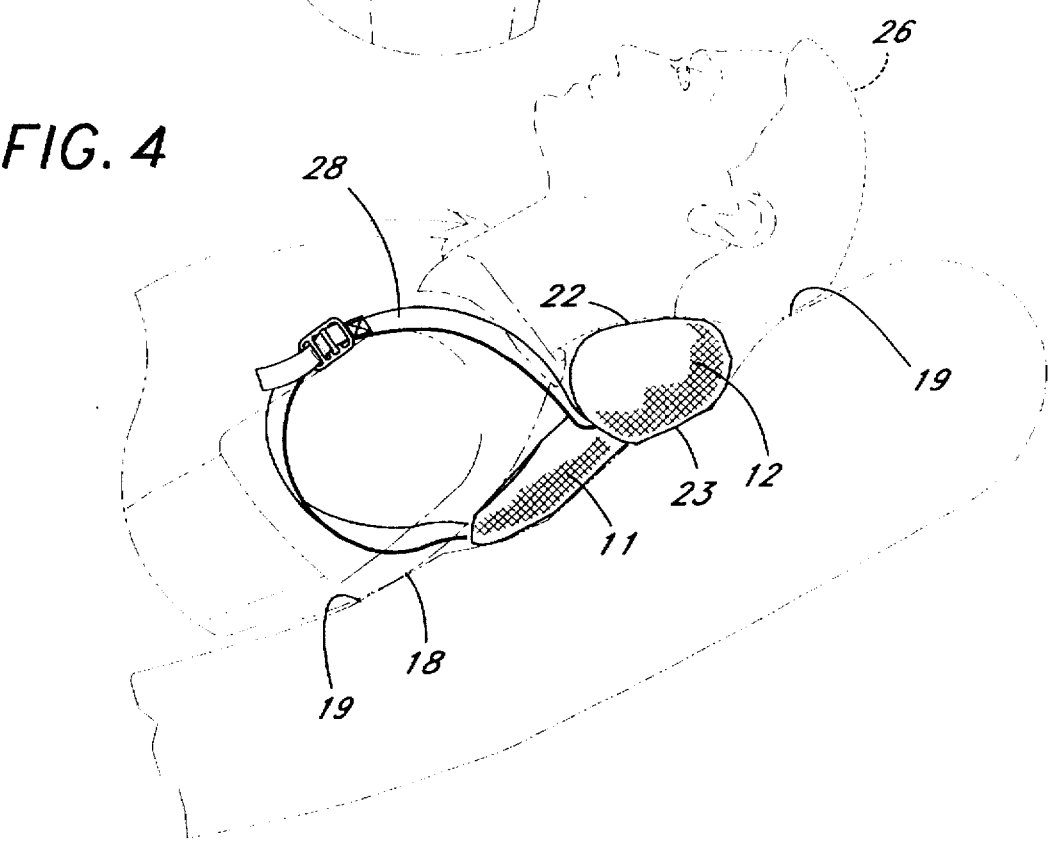
FIG. 4 is a left side view of the upper spine and neck support cushion of FIG. 1 shown on a wearer in a reclining position.

The generally vertical spine support pillow 11 lies upon the back of the wearer on the first four to five vertebrae in the upper thoracic area between the shoulders. As the user lies on a reclining chair or a bed this cushion lifts the upper part of the spine for the specific purpose of allowing the shoulders to relax back to the supporting chair or bed surface. When lying in a prone position this feature allows the shoulders to relax to the surface of the chair or bed. The upper part of the thoracic portion of the wearer is indicated by reference character 17 in FIG. 2. The user in a reclined position is shown in FIG. 4 where it can be seen that the user's shoulders 18 are supported by chair surface 19 and not by any portion of the cushion of the present invention.

The generally horizontal neck support pillow 12 has a right side 20 and a left side 21 and is attached to the top 16 of generally vertical spine support pillow 11. Neck support 12 has a neck contacting surface 22 and a furniture contacting surface 23. Neck support pillow 12 has a top 24 and a bottom 25. The neck support pillow 12 is free of any head support portion as shown best in FIG. 4 where the wearer's head 26 can be seen to be supported by chair surface 19 and not by neck support pillow 12. Neck support pillow 12 is held beneath the cervical area of the neck. This offers a gentle support to the area keeping the neck in a natural non-flexed position. It is not intended to alter the natural curve of the neck, only to offer support in its natural position. Neck support pillow 12 is preferably at least 7" to about 12" long and preferably about 9" (8–10") long. It should have a diameter of from 3–6" and preferably about 5". The spine support pillow is made from any soft pliable material or could be inflatable or made from a heat retaining material.

Another important feature of the present invention is the back pack style straps consisting of right strap 27 and left strap 28. Right strap 27 has a top portion 29 affixed to the generally horizontal neck support pillow and a bottom portion 30 affixed near bottom 13 of generally vertical spine support pillow 11. A length adjusting means such as buckle 31 allow the user to adjust the strap to his or her comfort position. Similarly, left strap 28 has a top 32 affixed to neck support pillow 12 and a bottom 33 affixed near bottom 13 of spine support pillow 11. A buckle 34 allows for length adjusting. The straps 27 and 28 allow the cushion to stay in place when one changes body position during use. These back pack style straps allow the use of a regular pillow during sleep without dislodging the device. The straps keep the device in place for purposes of relaxing the shoulders when the subject returns to lying on the back. No assistance is required to put on or take off the support cushion of the present invention and it is, of course, very light in weight and comfortable to use. It can be used daily by people who experience mild to severe upper back and neck discomfort during the day.

The result is lightweight economical and easy to use cushion which provides substantial relaxation when used. It can be retained in place during sleep and can be easily put on or taken off when desired.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

I claim:

1. An upper spine and neck support cushion consisting essentially of:

a generally vertical spine support pillow having a length from about four inches to about eight inches, said spine support pillow having a bottom, a spine contacting surface, sides and a furniture contacting side and a top, said spine support pillow being constructed from a soft pliant material;

a generally horizontal neck support pillow attached to the top of said spine support pillow, said generally horizontal neck support pillow having a neck contacting surface and a furniture contacting surface, a top surface and a bottom surface, a right end and a left end, said neck support pillow being configured and sized to be free of any head support means whereby the user's head will be supported by the surface upon which a user may rest and not the neck support pillow; and means for holding said upper spine and neck support pillow to a human wearer wherein said means for holding said upper spine and neck support pillow to a human wearer comprises a right hand strap having a lower end affixed to said spine support pillow near the bottom thereof and an upper end affixed to a right hand side of said neck support pillow and a left hand strap having a lower end affixed to said spine support pillow near the bottom thereof and an upper end affixed to a left hand side of said neck support pillow and length adjusting means between the upper and lower ends of each strap.

* * * * *